United States Patent
Brubaker et al.

[11] Patent Number: 5,804,974
[45] Date of Patent: Sep. 8, 1998

[54] MATERIALS CHARACTERIZATION CELL FOR POLARIZATION SPECTRUM AND STREAMING ELECTRIFICATION MEASUREMENTS

[75] Inventors: Michael A. Brubaker; George K. Frimpong, both of Raleigh, N.C.

[73] Assignee: Abb Power T&D Company Inc., Raleigh, N.C.

[21] Appl. No.: 859,749

[22] Filed: May 21, 1997

Related U.S. Application Data

[62] Division of Ser. No. 484,571, Jun. 7, 1995.

[51] Int. Cl.$^6$ .......................... G01N 27/403; G01R 31/16
[52] U.S. Cl. .......................... 324/553; 324/450; 324/551; 324/698
[58] Field of Search .................... 324/425, 439, 324/450, 693, 698, 701, 707, 71.1, 76.19, 547, 551, 553

[56] References Cited

U.S. PATENT DOCUMENTS

| | | | |
|---|---|---|---|
| 3,866,114 | 2/1975 | Johnston | 324/452 |
| 4,594,553 | 6/1986 | Varga | 324/454 |
| 4,668,916 | 5/1987 | Pech | 324/456 |
| 4,758,962 | 7/1988 | Fernandes | 364/483 |
| 4,774,453 | 9/1988 | Dechene et al. | 324/453 |
| 4,777,381 | 10/1988 | Fernandes | 307/64 |
| 4,777,431 | 10/1988 | Day et al. | 324/690 |
| 4,785,233 | 11/1988 | Coleman | 324/605 |
| 4,818,930 | 4/1989 | Flemming et al. | 324/698 |
| 4,855,671 | 8/1989 | Fernandes | 324/127 |
| 4,857,829 | 8/1989 | Sagae et al. | 324/698 |
| 4,873,489 | 10/1989 | Melcher et al. | 324/453 |
| 4,947,468 | 8/1990 | Nelson | 324/453 |
| 5,017,879 | 5/1991 | Lucas et al. | 324/663 |
| 5,107,447 | 4/1992 | Ozawa et al. | 364/551.01 |
| 5,151,660 | 9/1992 | Powers et al. | 324/689 |
| 5,187,444 | 2/1993 | Kumada | 324/663 |
| 5,214,595 | 5/1993 | Ozawa et al. | 364/551.01 |
| 5,325,068 | 6/1994 | Rauf | 324/713 |
| 5,334,941 | 8/1994 | KIng | 324/637 |
| 5,341,101 | 8/1994 | Maerefat et al. | 324/639 |
| 5,370,776 | 12/1994 | Chen | 324/425 X |

*Primary Examiner*—Glenn W. Brown
*Attorney, Agent, or Firm*—Woodcock Washburn Kurtz Mackiewicz & Norris LLP

[57] ABSTRACT

A materials characterization test cell is disclosed. The test cell includes a housing including spacers for supporting sample insulation materials, and a channel disposed in the housing to permit the passage of oil through the housing. A pair of electrodes is provided to provide a mechanism for making polarization spectrum and/or streaming electrification measurements.

9 Claims, 4 Drawing Sheets

MATERIALS CHARACTERIZATION CELL FOR POLARIZATION SPECTRUM AND STREAMING ELECTRIFICATION MEASUREMENTS

This is a division of application Ser. No. 08/484,571, filed Jun. 7, 1995, the disclosure of which is herein incorporated by reference.

FIELD OF THE INVENTION

The present invention relates generally to the field of power transformers and insulation thereof, and more particularly to a materials characterization cell for measuring polarization spectra and streaming electrification characteristics of insulation materials and combinations of insulation materials and dielectric fluids.

BACKGROUND OF THE INVENTION

Polarization spectrum measurements provide information about the state of transformer insulation. Such measurements have the distinct advantage of being non-invasive and are thus ideal for field applications. The polarization spectrum is known to be dependent upon both aging and moisture content, which are of great interest to power transformer manufacturers. However, calibrating and understanding the dependencies of the polarization spectrum on the age and moisture content of insulation can be extremely difficult. One object of the present invention is to provide a materials characterization test cell that combines oil and cellulose insulation in a well-defined geometry, which test cell is useful in resolving the difficulty in calibrating and understanding said dependencies. The materials calibration test cell can be integrated into an external system to support oil flow and can also be used to examine streaming electrification.

Streaming electrification has been identified as a hazard for large forced-oil-cooled power transformers. This phenomenon is traditionally quantified by measuring the electrostatic charging tendency (ECT) of the transformer oil. However, this measurement is conventionally made by passing the oil through a filter and does not address the physical process occurring in a transformer. Another objective of the present invention is to provide a materials characterization test cell and method of use thereof for determining the charging tendency of a liquid/solid insulation combination. The invention employs the novel test cell, which allows a dielectric liquid to flow against solid insulation samples in a well-defined geometry. The charging tendencies of various transformer insulation components can be easily determined with the present invention.

Polarization Spectrum

The polarization spectrum as a function of the energizing frequency encompasses a wide range of physical phenomena. At very high (optical) frequencies, electron behavior is evident while at very low (DC) frequencies, space and surface charge effects dominate. For transformer diagnostics, the latter case is of interest since the spectrum can provide information about the state of the insulation in the transformer. The degree of insulation aging and moisture content both significantly influence the polarization spectrum, and therefore the spectrum is indicative of the age and moisture content of the insulation.

A dielectric material will be polarized by the application of an electric field. One method of characterizing polarization is through the recovery voltage method (RVM). The geometric capacitance of the insulation causes the build-up of a charge which is discharged after the sample is energized with a DC voltage for a specified period of time. The voltage appearing across a dielectric is measured once the short circuit is opened. The spectrum is obtained by sweeping the energizing and short circuit times over the range of interest. The peak recovery voltage is measured over this range, and the recovery voltage characteristic typically exhibits a peak whose location and magnitude vary with the insulation properties. Typical results for transformer polarization spectra show that cellulose aging and/or moisture content can shift the recovery voltage peak.

A polarization spectrum analyzer (e.g., one made by TETTEX) can be readily attached to the bushing of a transformer. This non-invasive analyzer provides only a macroscopic characteristic of a very large and complex insulation structure. The results are thus difficult to explain and understand in terms of the microscopic physical phenomena of interest. The materials characterization test cell provided by the present invention provides an ideal mechanism for microscopically studying the very large and complex insulation structure employed by a transformer. The invention provides a well-defined oil/cellulose system that can be examined under very controlled conditions with both static and flowing oil. The cell geometry allows for different solid samples over a range of thickness to be easily installed and tested.

Streaming Electrification

Despite strict industrial specifications, transformer oils may contain trace amounts of impurities. When such impurities are dissociable in nature, positive and negative ions may be formed. If the oil is placed in contact with a solid material, one ionic species will be preferentially adsorbed. As a result of such adsorption, an excess of the other species will remain in the oil. Under static conditions, these excess charges occupy a Boltzmann distribution near their counterparts at the liquid/solid interface. This double layer at the interface is established in accordance with the static relaxation equation such that charge is conserved.

When the oil is circulated for cooling purposes, the entrained ions are convected away from the counterions adsorbed in the solid. Static potentials may be generated, which can compromise the dielectric integrity of the transformer. This phenomenon is traditionally quantified in terms of the oil. The ECT can be determined by passing the oil through a filter and measuring the resulting streaming current. The ECT for the oil can then be calculated based upon the flow rate. The degree of streaming electrification for various oils can be compared in this manner.

The disadvantage of the known method for performing ECT measurements is that the role of the solid phase is not adequately addressed. In reality, the nature of the cellulose surface may significantly influence the electrification process. Furthermore, the flow conditions existing in a filter are much different from those in a transformer duct. The present invention provides a mechanism for obtaining charging tendency measurements of a liquid/solid dielectric system, and the geometry allows solid samples to be easily installed for testing against various transformer oils in a plane channel geometry. The invention provides a much more realistic assessment of streaming electrification in power transformer insulation.

SUMMARY OF THE INVENTION

A materials characterization cell in accordance with the present invention comprises a housing, a channel disposed in the housing to permit the static or dynamic passage of oil through the housing, a first sample of insulation material disposed in the housing adjacent to the channel, and a first electrode disposed in the housing adjacent to the first sample. The presently preferred embodiment of the invention also includes a second sample of the insulation material disposed in the housing adjacent to the channel and opposite the first sample, and a second electrode disposed in the housing adjacent to the second sample. This embodiment provides a capacitor having a prescribed geometry, which is formed by the electrodes, samples, and channel.

The present invention also provides a materials characterization system including a materials characterization cell as described above, and a polarization spectrum analyzer coupled to the materials characterization cell. The presently preferred embodiment of the system also includes a means for providing a controlled flow of oil through the materials characterization cell.

An alternative preferred embodiment of the present invention comprises an electrometer instead of or in addition to the polarization spectrum analyzer. This embodiment is employed to measure the charging tendency of a combination of liquid and solid insulation materials. In one exemplary embodiment of the present invention, the electrometer is accurate to within $0.1 \times 10^{-12}$ A and has a settling time of approximately 1 second. A Keithbly model 617 or similar electrometer may be used to carry out the present invention.

Other features and advantages of the present invention are disclosed below.

DETAILED DESCRIPTION OF PREFERRED EMBODIMENTS

Figure 1:
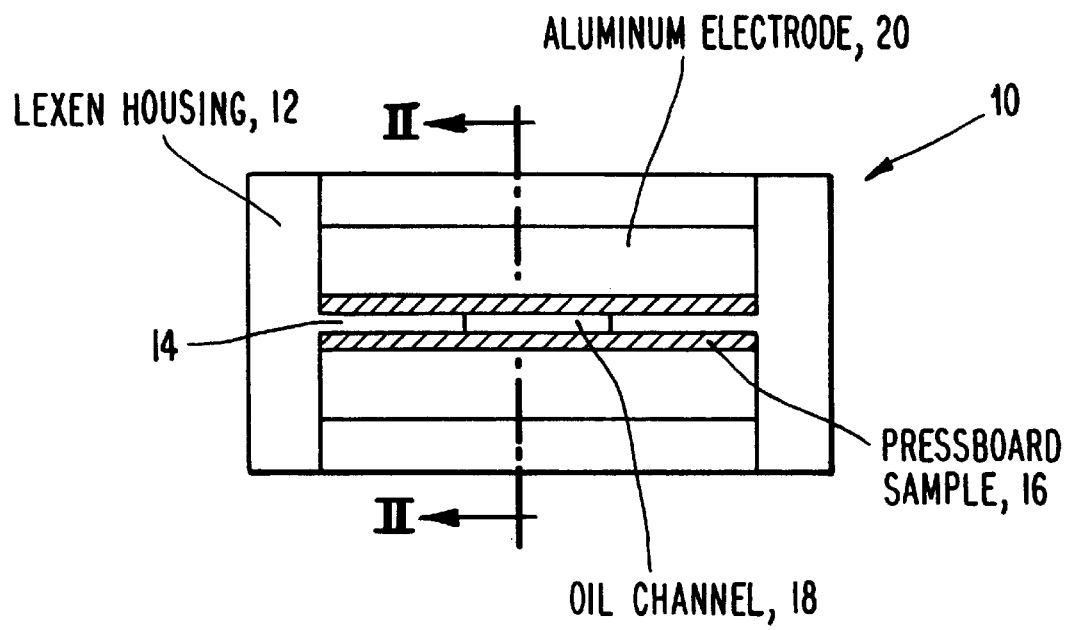
FIG. 1 depicts an end view of a materials characterization cell in accordance with the present invention.
Figure 2:
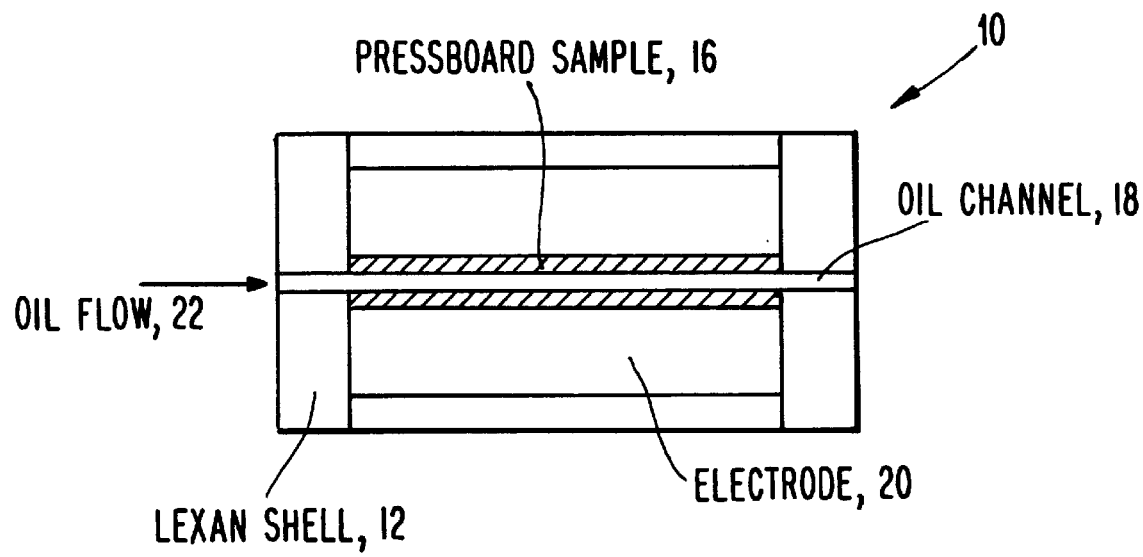
FIG. 2 depicts a side view of the materials characterization cell of FIG. 1.

One presently preferred embodiment of the materials characterization cell in accordance with the present invention is depicted in FIGS. 1 and 2. As shown, the inventive materials characterization cell 10 comprises a LEXAN housing 12 including spacer portions 14, cellulose or press board samples 16, a channel 18, and aluminum electrodes 20. The LEXAN spacers 14 support the samples 16 such that the geometry of the channel 18 is independent of the sample thickness. As indicated by the arrow in FIG. 2, the channel 18 allows for the passage of oil 22 through the cell 10. Oil can flow through the cell in either direction, i.e., in the direction of the arrow or in the opposite direction.

Figure 3:
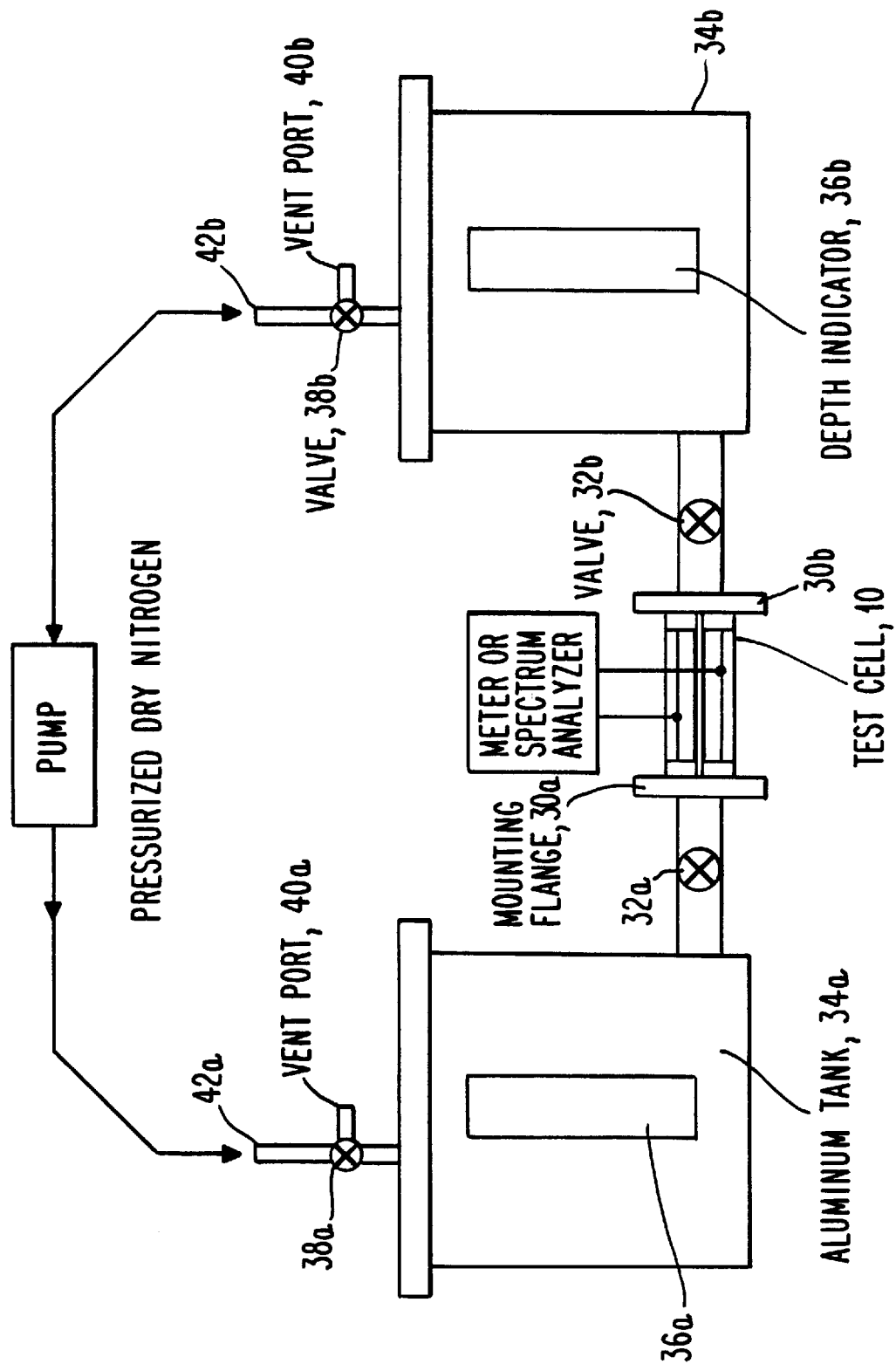
FIG. 3 schematically depicts a materials characterization system in accordance with the present invention.

FIG. 3 depicts one presently preferred embodiment of a materials characterization system in accordance with the present invention. As shown, this system employs the test cell 10; a pair of mounting flanges 30a, 30b; a pair of valves 32a, 32b; a pair of aluminum tanks 34a, 34b; depth gauges or indicators 36a, 36b for the respective tanks; a second pair of valves 38a, 38b; a pair of vent ports 40a, 40b associated with the valves 38a, 38b; and inlet/outlet ports 42a, 42b. The two identical tanks 34a, 34b are employed as oil reservoirs. The flange arrangement is provided to facilitate installation of the cell 10. Oil is forced through the cell by pressurizing one tank with dry nitrogen and venting the other to atmosphere. The depth gauges 36a, 36b provide a mechanism for measuring the volume of oil dispensed through the cell 10, which is timed such that the flow rate can be estimated. Typical oil velocities are on the order of 1 meter per second and the flow is laminar with a Reynolds number of approximately 200. The dimensions of the materials characterization cell 10 provide for fully developed flow over most of the length of the oil channel 18. A polarization spectrum analyzer (or suitable electrometer for streaming electrification measurements, as discussed below) can be connected across the cell electrodes 20.

In light of the long times required for polarization spectrum measurements, a pump may be added to sustain a steady flow of oil over the course of the experiment. The pump may be installed in series with the reservoir tanks to complete a hydraulic circuit. Any charges generated due to the streaming electrification in the pump will thus be allowed to relax in the tanks before the oil enters the cell 10. In this manner, the influence of flow dynamics upon the polarization spectrum may be investigated as a function of insulation material and thickness.

Figure 4:
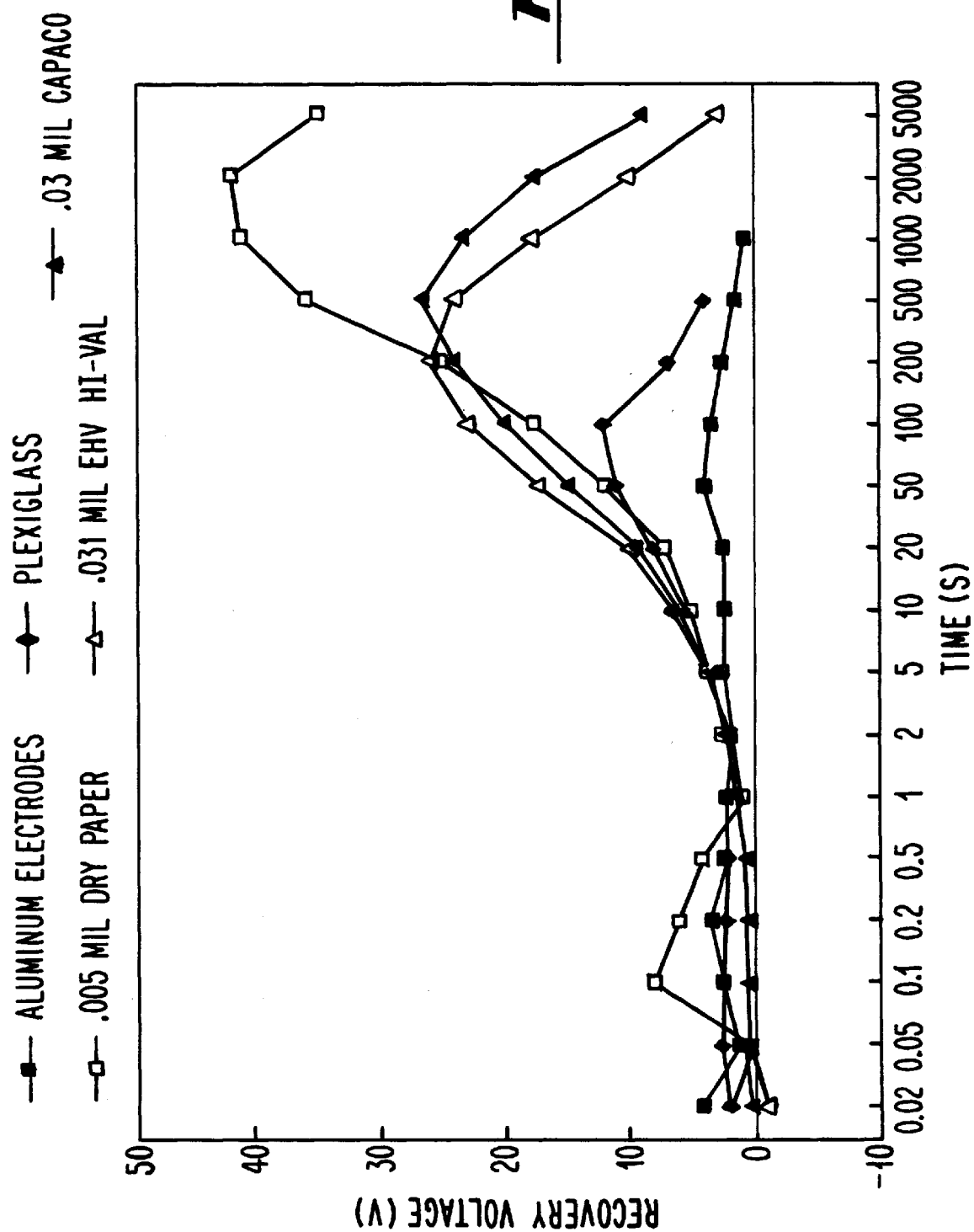
FIG. 4 is a plot of recovery voltage over time (i.e., the polarization spectrum) for various material types and thicknesses, as determined by a polarization spectrum analyzer. The data depicted in this plot were obtained with a materials characterization test cell in accordance with the present invention.

FIG. 4 depicts polarization spectra obtained with the system of FIG. 3, for aluminum electrodes, plexiglass, 0.03 mil capaco, 0.005 mil dry paper, and 0.031 mil EHV Hi-Val insulation materials. All of these materials, except for bare aluminum, are dielectrics. The listed dielectrics are types of insulation used in transformers. FIG. 4 demonstrates the polarization spectrum associated with each material (in oil). This data can be used to evaluate the state of insulation over time.

The materials characterization cell 10 described above employs electrodes 20 that are fitted with O rings to provide a seal and are secured with DELRIN compression bolts. As discussed above, the cell dimensions are selected to provide for fully developed flow over most of the channel length. Streaming current measurements can be obtained from the aluminum electrodes 20 using a suitable electrometer. The cell is preferably shielded with a Faraday cage such that currents in the picoampere range can be measured reliably. Based on the calculated flow rate Q, the charging tendency of a given oil/cellulose combination is determined in terms of the streaming current I as q=I/Q. The charging tendency can be evaluated in terms of the solid sample material, thickness, and surface characteristics for various transformer oils or other dielectric liquids. The solid samples may be supplied in sheet form and machined to fit into the cell.

Figure 5:
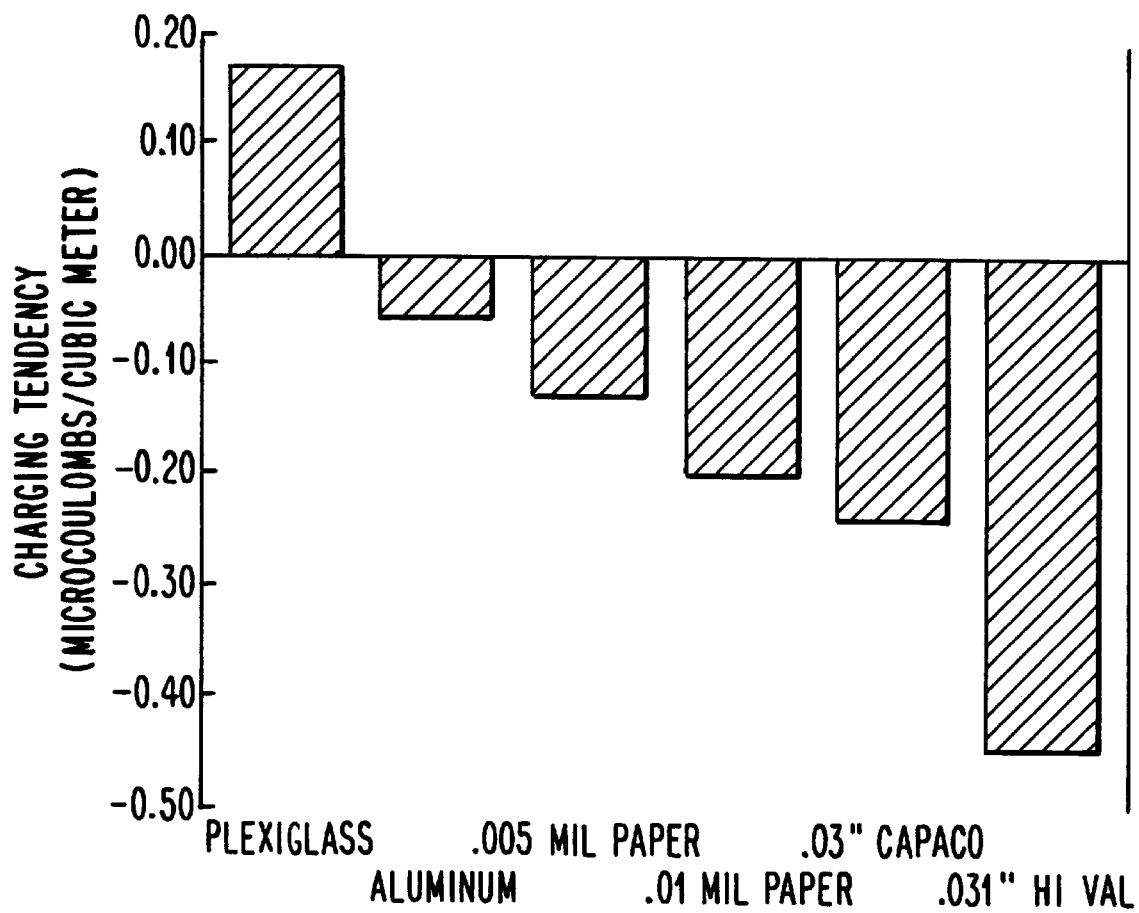
FIG. 5 is a plot of the ECT of various materials as determined with the materials characterization cell of the present invention. This plot shows that streaming electrification is a function of the solid insulation component in addition to the liquid, which in this case was Exxon Univolt Transformer Oil.

FIG. 5 depicts the results of charging tendency measurements obtained with the system depicted in FIG. 3. The results show that streaming electrification is clearly a function of the solid insulation component and the liquid.

It should be noted that the scope of protection following claims is not limited to the presently preferred embodiments described above. For example, the cell could be made a different size. A larger size with a higher flow rate would yield higher signals for measurement.

We claim:

1. A materials characterization system, comprising:
   (a) a materials characterization cell;
   (b) a polarization spectrum analyzer coupled to said materials characterization cell; and
   (c) means for providing a controlled flow of oil through said materials characterization cell.

2. A materials characterization system as recited in claim 1, wherein said materials characterization cell comprises a housing; a channel disposed in said housing, said channel permitting the passage of oil through said housing; a first sample of insulation material disposed in said housing adjacent to said channel; and a first electrode disposed in said housing adjacent to said first sample.

3. A materials characterization system as recited in claim 2, wherein said materials characterization cell further comprises a second sample of said insulation material, said second sample being disposed in said housing adjacent to said channel and opposite said first sample; and a second electrode disposed in said housing adjacent to said second sample.

4. A method for obtaining a polarization spectrum of a sample of insulation material for use in an oil filled transformer, said polarization spectrum being indicative of the age and moisture content of said sample, comprising the steps of:
   (a) disposing said sample in a materials characterization cell;
   (b) coupling a polarization spectrum analyzer to said materials characterization cell; and
   (c) obtaining said spectrum with said analyzer.

5. A method as recited in claim 4, wherein said materials characterization cell comprises a housing; a channel disposed in said housing, said channel permitting the passage of oil through said housing; said sample of insulation material disposed in said housing adjacent to said channel; and a first electrode disposed in said housing adjacent to said sample.

6. A method as recited in claim 5, wherein said materials characterization cell further comprises a second sample of said insulation material, said second sample being disposed in said housing adjacent to said channel; and a second electrode disposed in said housing adjacent to said second sample.

7. A method for determining the charging tendency of a combination of liquid and solid insulation materials, comprising the steps of:
   (a) disposing a sample of a solid insulation material in a materials characterization cell;
   (b) passing a dielectric liquid through said materials characterization cell;
   (c) measuring a streaming current associated with said dielectric liquid with a meter coupled to said materials characterization cell; and
   (d) determining the charging tendency on the basis of the flow rate of the liquid dielectric and the measured streaming current.

8. A method as recited in claim 7, wherein said materials characterization cell comprises a housing; a channel disposed in said housing, said channel permitting the passage of said liquid dielectric through said housing; said sample of insulation material disposed in said housing adjacent to said channel; and a first electrode disposed in said housing adjacent to said sample.

9. A method as recited in claim 8, wherein said materials characterization cell further comprises a second sample of said insulation material, said second sample being disposed in said housing adjacent to said channel; and a second electrode disposed in said housing adjacent to said second sample.

* * * * *